United States Patent
Cho et al.

(10) Patent No.: US 7,230,105 B2
(45) Date of Patent: Jun. 12, 2007

(54) 9-AMINOACRIDINE DERIVATIVES AND PROCESS FOR THE PREPARATION THEREOF

(75) Inventors: Eui-Hwan Cho, Seoul (KR); Sun-Gan Chung, Kyungki-do (KR); Sun-Hwan Lee, Kyungki-do (KR); Ho-Seok Kwon, Kyungki-do (KR); Dong-Wook Kang, Kyungki-do (KR)

(73) Assignee: Samjin Pharmaceutical Co., Ltd. (KR)

( * ) Notice: Subject to any disclaimer, the term of this patent is extended or adjusted under 35 U.S.C. 154(b) by 298 days.

(21) Appl. No.: 10/507,153

(22) PCT Filed: Mar. 7, 2002

(86) PCT No.: PCT/KR02/00392

§ 371 (c)(1),
(2), (4) Date: Sep. 7, 2004

(87) PCT Pub. No.: WO03/074490

PCT Pub. Date: Sep. 12, 2003

(65) Prior Publication Data

US 2005/0222167 A1 Oct. 6, 2005

(51) Int. Cl.
*C07D 401/12* (2006.01)
*C07D 219/12* (2006.01)
*A61K 31/496* (2006.01)

(52) U.S. Cl. ............... 544/361; 544/360; 546/105; 514/252.03; 514/297

(58) Field of Classification Search ............... 546/105; 544/360, 361; 514/252.03, 297
See application file for complete search history.

(56) References Cited

U.S. PATENT DOCUMENTS

| 4,575,553 | A | * | 3/1986 | Kavadias et al. | ............ 546/106 |
| 5,229,395 | A | * | 7/1993 | Watanabe et al. | ............ 514/297 |
| 5,354,864 | A | * | 10/1994 | Watanabe et al. | ............ 546/106 |
| 2002/0111491 | A1 | * | 8/2002 | Cho et al. | .................. 546/105 |

FOREIGN PATENT DOCUMENTS

| WO | WO91/05770 | * | 5/1991 |
| WO | WO 00/37447 | * | 6/2000 |

OTHER PUBLICATIONS

Analysis and stability of a novel, anticancer agent, SJ-8029, possessing microtubute and topoisomerase inhibiting activitites Cho Chang et al Jun. 2002.*

* cited by examiner

*Primary Examiner*—Rita Desai
(74) *Attorney, Agent, or Firm*—Anderson Kill & Olick, PC

(57) ABSTRACT

The present invention relates to a new 9-aminoacridine derivative which exhibits prominent antitumor activity and low toxicity.

3 Claims, No Drawings

9-AMINOACRIDINE DERIVATIVES AND PROCESS FOR THE PREPARATION THEREOF

BACKGROUND OF THE INVENTION

1. Field of the Invention

The present invention relates to a new 9-aminoacridine derivative of the general formula (I)

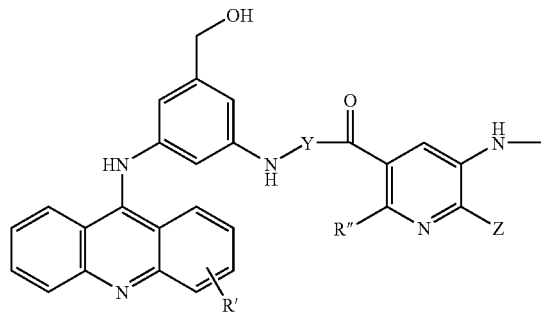

2. Description of the Prior Art

WO 00/37447 describes 9-amnoacridine derivatives and process for the preparation thereof of the compounds of the formula (1)

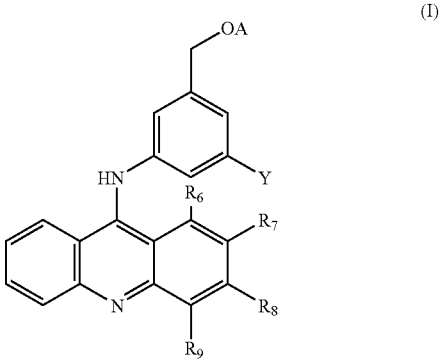

wherein A is hydrogen or

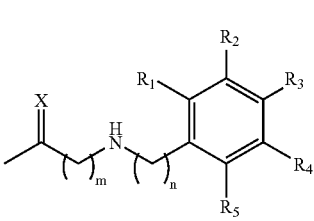

wherein Y is a bond or

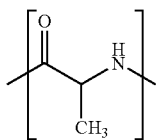

(wherein X is oxygen or sulfur, $R_1$, $R_2$, $R_3$, $R_4$ and $R_5$ are independently hydrogen, halogen, nitro, amino, hydroxy, $C_1$–$C_4$ lower alkylhydroxy, $C_1$–$C_4$ lower alkoxy, R' and R" are independently $C_1$–$C_4$ alkyl or $C_1$–$C_4$ lower alkoxy, and Z is $C_1$–$C_4$ lower alkyl, $C_1$–$C_4$ lower alkoxy or $C_1$–$C_4$ lower alkylamino.

In the above definitions, $C_1$–$C_4$ lower alkyl means straight or branched alkyl groups such as methyl, ethyl, propyl, isopropyl, n-butyl, isobutyl, sec-butyl or the like.

$C_1$–$C_4$ lower alkoxy means methoxy, ethoxy, propoxy, isopropoxy, butoxy, isobutoxy, tert-butoxy or the like.

$C_1$–$C_4$ lower alkylamino means methylamino, ethylamino, propylamino, butylamino or the like.

(wherein X is oxygen or sulfur, R1, R2, R3, R4 and R5 are independently hydrogen, halogen, nitro, amino, hydroxy, C1–C4 lower alkylhydroxy, C1–C4 lower alkylamino, C1–C8 alkyl, C1–C4 lower alkoxy or C1–C4 lower alkyloxycarbonyl and m and n are independently an integer of 0, 1 or 2.), R6, R7, R8 and R9 are independently C1–C8 alkyl or C1–C4 lower alkoxy, and Y is hydrogen, amino, —N=CHR' (wherein R' is hydrogen, benzyl, C1–C8 alkyl or C1–C6 lower alamino),

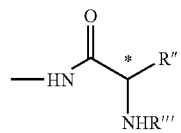

(wherein R" is hydrogen, benzyl, C1–C8 alkyl or C1–C6 lower alkylamino, and R'" is hydrogen, benzyl, C1–C8 alkyl or amino protecting group) or

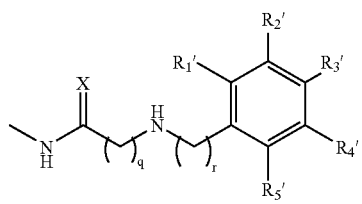

(wherein, X is as defined above, R1', R2', R3', R4' and R5' are independently hydrogen, halogen, nitro, amino, hydroxy, C1–C4 lower alkylhydroxy, C1–C4 lower alkylamino, C1–C8 alkyl, C1–C4 lower alkoxy or C1–C4 lower alkyloxycarbonyl, and q and r are independently an integer of 0, 1 or 2) or its pharmaceutically acceptable salt, and process for the preparation thereof.

In the above compounds of the formula (I) wherein Y is

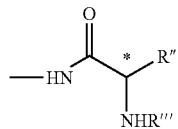

(R" and R'" are as defined above.), there may be isomers of l-form, d-form or racemic form.

However, the compound of the present invention does not describe in the WO 00/37447.

SUMMARY OF THE INVENTION

The inventors had studied for a long time to find new compounds having intensive antitumor activities. As a result, the inventors have found out that the compounds of the general formula (I), or acid addition salts thereof as defined above have not only prominent antitumor activities but also very low toxicities.

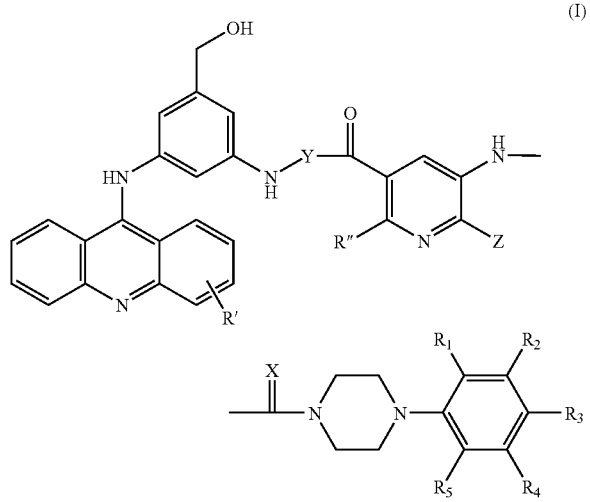

wherein Y is a bond or

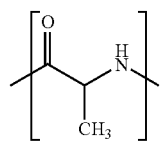

(wherein X is oxygen or sulfur, $R_1$, $R_2$, $R_3$, $R_4$ and $R_5$ are independently hydrogen, halogen, nitro, amino, hydroxy, $C_1$–$C_4$ lower alkylhydroxy, $C_1$–$C_4$ lower alkylamino, $C_1$–$C_8$ allyl or $C_1$–$C_4$ lower alkoxy, R' and R" are independently $C_1$–$C_8$ alkyl or $C_1$–$C_4$ lower alkoxy, and Z is $C_1$–$C_4$ lower alkyl, $C_1$–$C_4$ lower alkoxy or $C_1$–$C_4$ lower alkylamino.

Accordingly, an object of the invention is to provide a compound of the general formula (I) or acid addition salt thereof having not only prominent antitumor activity but also very low toxicity.

Another object of the invention is to provide a process for the preparation of the compound of the general formula (I) or acid addition salt thereof.

The compounds of the present invention can be mixed with pharmaceutically acceptable vehicles by a conventional method to give pharmaceutical preparations to be used for prevention or treatment of various kinds of tumors.

Therefore, the other object of the present invention is to provide pharmaceutical preparations containing an effective amount of a compound of the general formula (I) or acid addition salt thereof as an active ingredient.

Acids which can be reacted with the compound of the general formula (I) to form acid addition salt thereof are pharmaceutically acceptable inorganic acids, organic acids, amino acids or sulfonic acids; for example, inorganic acids such as hydrochloric acid, hydrobromic acid, sulfuric acid, phosphoric acid and nitric acid; organic acids such as formic acid, acetic acid, propionic acid, succinic acid, citric acid, maleic acid and malonic acid; amino acids such as serine, cysteine, cystine, asparagine, glutamine, lysine, arginine, tyrosine and proline; sulfonic acids such as methanesulfonic acid, ethanesulfonic acid, benzenesulfonic acid and toluenesulfonic acid.

Vehicles used in formulating pharmaceutical preparations containing the compound of the general formula (I) as an active ingredient are sweetening agents, binding agents, dissolving agents, aids for dissolution, wetting agents, emulsifying agents, isotonic agents, adsorbents, degrading agents, antioxidents, preservatives, lubricating agents, fillers, perfume or the like; for example may include lactose, dextrose, sucrose, mannitol, sorbitol, cellulose, glycine, silica, talc, stearic acid, stearin, magnesium stearate, calcium stearate, magnesium aluminum silicate, starch, gelatine, tragacanth gum, alginic acid, sodium alginate, methyl cellulose, sodium carboxy methyl cellulose, agar, water, ethanol, polyethylenglycol, polyvinyl pyrrolidone, sodium chloride, potassium chloride, orange essence, strawberry essence and vanilla aroma.

Daily dosage of the compound of the general formula (I) may be varied depending on age, sex and degree of disease, but preferably ling to 5,000 mg per day may be administered by once to several times.

DETAIL DESCRIPTION OF THE PREFRRED EMBODIMENT(S)

The compound of the general formula (I) according to the present invention may be prepared by following schemes I, II.

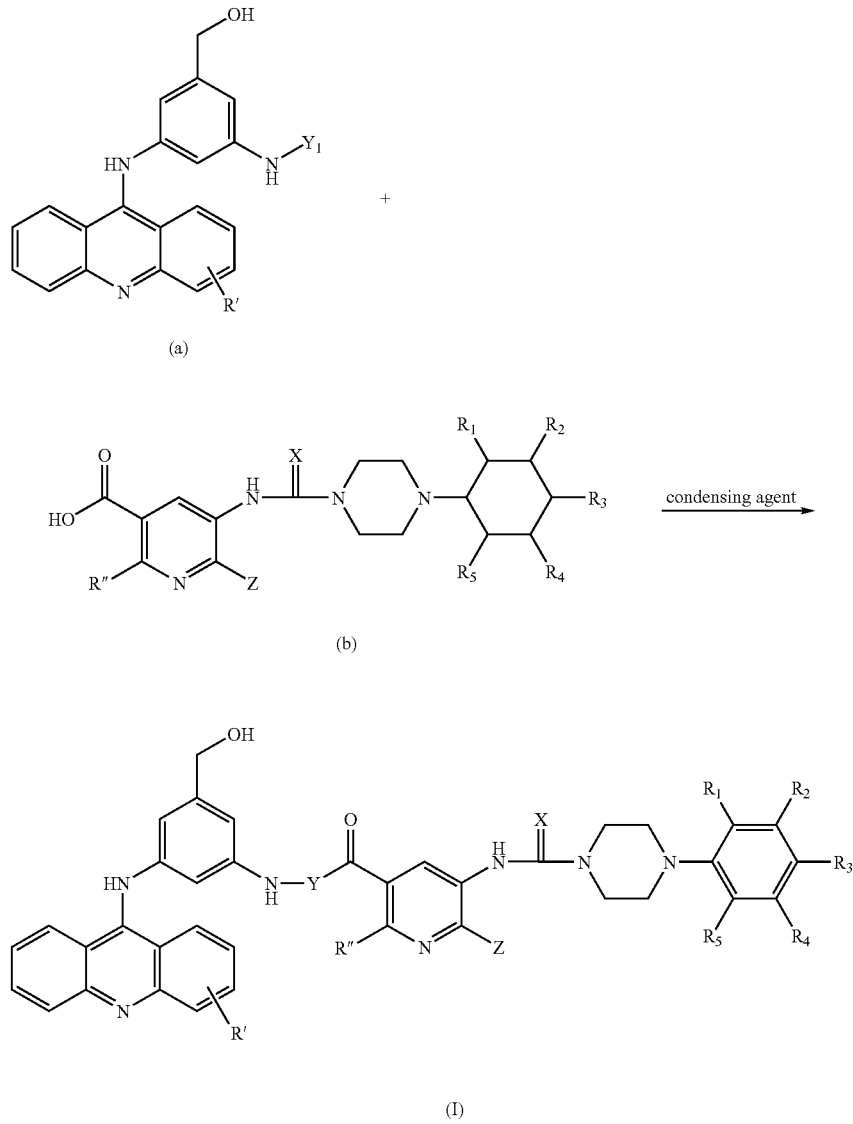

wherein $R_1$, $R_2$, $R_3$, $R_4$ and $R_5$, R', R", X, Y and Z are as defined above and $Y_1$ is hydrogen or the group of

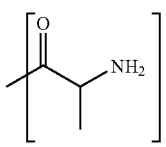

The compound of the general formula (a) and (b) are reacted under the presence of condensing agent and acid in a conventional organic solvent to give effectively a comound of the general formula (I).

The reaction may be carried out preferably in a conventional organic solvent such as tetrahydrofuran, dichloromethane, chloroform, acetonitrile, dimethylformamide, pyridine, etc.

The reaction may be carried out preferably under the presence of condensing agent such as dicyclohexylcarbodiimide(DCC), HOBT or WSCD in a conventional acid such as inorganic acid or organic acid.

A compound of the general formula (a) or (b) is a known compound in J. Med. Chem., 1995, 38, 3226 or in PCT/KR99/00787 or can be prepared and used by a analogy method thereof.

The reaction may be carried out at a temperature between 3° C. and a boiling point of a solvent, preferably 25° C. and 50° C. for a time between 5 and 24 hours, preferably for a time between 10 and 24 hours.

Acid may be used 1~1.5 equivalent, preferably 1~1.1 equivalent.

Scheme II

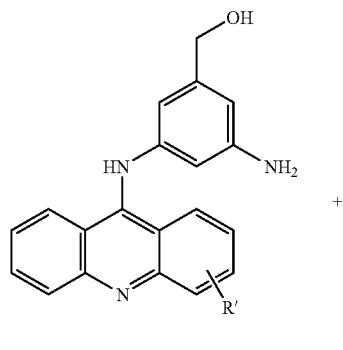

(c)

+

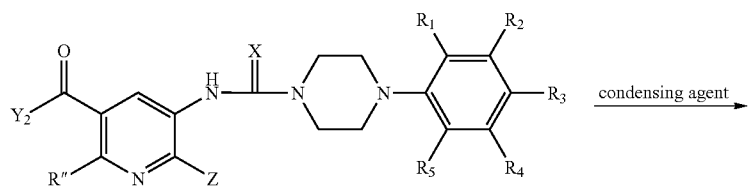

(d)

condensing agent

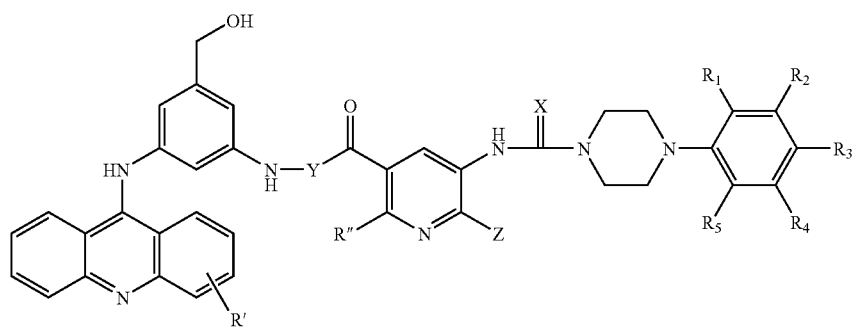

(I)

wherein $R_1, R_2, R_3, R_4, R_5, R', R'', X, Y$ and $Z$ are as defined above and $Y_2$ is —OH or the group of

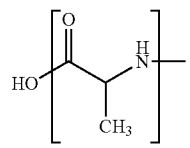

The compound of the general formula (c) and (d) are reacted under the presence of condensing agent and acid in a conventional organic solvent to give effectively a comound of the general formula (I).

The reaction may be carried out preferably in a conventional organic solvent such as tetrahydrofuran, dichloromethane, chloroform, acetonitrile, dimethylformamide, pyridine, etc.

The reaction may be carried out preferably under the presence of condensing agent such as dicyclohexylcarbodiimide(DCC), HOBT or WSCD in a conventional acid such as inorganic acid or organic acid.

A compound of the general formula (c) or (d) is a known compound in J. Med. Chem., 1995, 38, 3226 or in PCT/KR99/00787 or can be prepared and used by a analogy method thereof.

The reaction may be carried out at a temperature between 3° C. and a boiling point of a solvent, preferably 25° C. and 50° C. for a time between 5 and 24 hours, preferably for a time between 10 and 24 hours.

Acid may be used 1~1.5 equivalent, preferably 1~1.1 equivalent.

EXAMPLES

Compounds of the general formula (I) were prepared according to the above-mentioned processes of the invention.

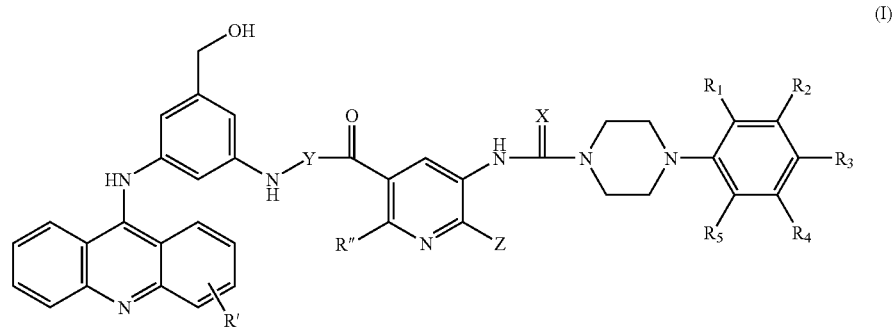

Examples 1~17

Compound of the General Formula (I) wherein

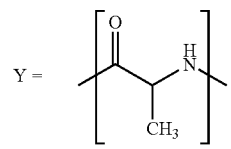

| Ex. No. | R' | R" | $R_1$ | $R_2$ | $R_3$ | $R_4$ | $R_5$ | X | Z |
|---|---|---|---|---|---|---|---|---|---|
| 1 | H | $CH_2CH_3$ | H | H | H | H | H | O | $OCH_3$ |
| 2 | H | $CH_2CH_3$ | H | $CH_3$ | H | $CH_3$ | H | O | $OCH_3$ |
| 3 | H | $CH_2CH_3$ | H | $OCH_3$ | H | $OCH_3$ | H | O | $OCH_3$ |
| 4 | H | $CH_2CH_3$ | H | F | H | F | H | O | $OCH_3$ |
| 5 | H | $CH_2CH_3$ | H | Cl | H | Cl | H | O | $OCH_3$ |
| 6 | H | $CH_2CH_3$ | H | F | H | H | H | O | $OCH_3$ |
| 7 | H | $CH_2CH_3$ | H | OH | H | OH | H | O | $OCH_3$ |
| 8 | H | $CH_2CH_3$ | H | $OCH_3$ | $OCH_3$ | $OCH_3$ | H | O | $OCH_3$ |
| 9 | H | $CH_2CH_2CH_3$ | H | $OCH_3$ | H | $OCH_3$ | H | O | $OCH_3$ |
| 10 | H | $CH_2CH_2CH_3$ | H | $CH_3$ | H | $CH_3$ | H | O | $OCH_3$ |
| 11 | H | $CH_3$ | H | $OCH_3$ | H | $OCH_3$ | H | S | $OCH_3$ |
| 12 | H | $CH_2CH_3$ | H | $OCH_3$ | H | $OCH_3$ | H | S | $OCH_3$ |
| 13 | H | $CH_2CH_2CH_3$ | H | $OCH_3$ | H | $OCH_3$ | H | S | $OCH_3$ |
| 14 | H | $CH_2CH_3$ | H | $CH_3$ | H | $CH_3$ | H | S | $OCH_3$ |
| 15 | 2-$CH_3$ | $CH_2CH_3$ | H | $CH_3$ | H | $CH_3$ | H | O | $OCH_3$ |
| 16 | 3,4-$CH_3$ | $CH_2CH_3$ | H | $CH_3$ | H | $CH_3$ | H | O | $OCH_3$ |
| 17 | 4-$OCH_3$ | $CH_2CH_3$ | H | $CH_3$ | H | $CH_3$ | H | O | $OCH_3$ |

EXAMPLE 18~29

Compound of the General Formula (I) wherein

Y=0(zero)

| Ex. No. | R' | R" | $R_1$ | $R_2$ | $R_3$ | $R_4$ | $R_5$ | X | Z |
|---|---|---|---|---|---|---|---|---|---|
| 18 | H | $CH_2CH_3$ | H | H | H | H | H | O | $OCH_3$ |
| 19 | H | $CH_2CH_3$ | H | $CH_3$ | H | $CH_3$ | H | O | $OCH_3$ |
| 20 | H | $CH_2CH_3$ | H | $OCH_3$ | H | $OCH_3$ | H | O | $OCH_3$ |
| 21 | H | $CH_2CH_3$ | H | F | H | F | H | O | $OCH_3$ |
| 22 | H | $CH_2CH_3$ | H | Cl | H | Cl | H | O | $OCH_3$ |
| 23 | H | $CH_2CH_3$ | H | F | H | H | H | O | $OCH_3$ |
| 24 | H | $CH_2CH_3$ | H | OH | H | OH | H | O | $OCH_3$ |
| 25 | H | $CH_2CH_3$ | H | $OCH_3$ | $OCH_3$ | $OCH_3$ | H | O | $OCH_3$ |
| 26 | H | $CH_2CH_3$ | H | $OCH_3$ | H | $OCH_3$ | H | S | $OCH_3$ |
| 27 | H | $CH_2CH_3$ | H | $CH_3$ | H | $CH_3$ | H | S | $OCH_3$ |
| 28 | H | $CH_2CH_3$ | H | F | H | H | H | S | $OCH_3$ |
| 29 | H | $CH_2CH_3$ | H | Cl | H | Cl | H | S | $OCH_3$ |

Example 1

4-phenylpiperazine-1-carboxylic acid (5-{1-[3-(acridine-9-yl-amino)-5-hydroxymethylphenylcarbamoyl]-ethylcarbamoyl}-6-methyl-2-methoxypyridine-3-yl)amide 2-ethyl-6-methoxy-5-[(4-phenylpiperazine-1-carbonyl) amino]nicotinic acid(0.5 g, 1.24 mmole) was dissolved in pyridine(30 mL) and thereto DCC(0.26 g, 1.24 nmole), DMAP(0.15 g, 1.24 mmole) and N-[3-(acridine-9-yl-amino)-5-hydroxymethyl-phenyl]-2-aminopropaneamide were added. After stirring the resulting mixture for 24 hours at the room temperature. The resulting product was purified by column chromatography to give the titled compound.

yield: 68.2% m.p.: 218220° C. $^1$H NMR(DMSO-$d_6$): 1.20(3H,t), 1.38(3H,d), 2.79(2H,q), 3.19(4H,m), 3.61(4H,m), 3.96(3H,s), 4.45(2H,s), 4.53(1H,m), 6.50(1H,m), 6.85(1H,t), 7.01(4H,d), 7.28(4H,m), 7.62(4H,m), 8.00(3H,d), 8.51(1H,d), 9.97(1H,s)

Example 2

4-(3,5-dimethylphenyl)piperazine-1-carboxylic acid (5-{1-[3-(acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3,5-dimethylphenyl)-piperazine-1-carbonyl]-amino}-6-methoxy-nicotinic acid and N-[3-(acridine-9-yl-amino)-5-hydroxymethyl-phenyl]-2-aminopropaneamide to give the titled compound.

yield: 52.3% m.p. 205207° C.

$^1$H NMR(DMSO-$d_6$): 1.20(3H,t), 1.38(3H,d), 2.79(2H,q), 3.19(4H,m), 3.59(4H,m), 3.75(6H,s), 3.96(3H,s), 4.45(2H,s), 4.53(1H,m), 5.18(1H/m), 6.03(1H,s), 6.14(2H,s), 6.48(1H,s), 7.01(2H,m), 7.30(3H,m), 7.56(3H,m), 7.96(2H,d), 8.18(1H,m), 8.50(1H,d), 9.95(1H,s)

Example 3

4-(3,5-dimethoxyphenyl)piperazine-1-carboxylic acid (5-{1-[3-(acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3,5-dimethoxyphenyl)-piperazine-1-carbonyl]-amino}-6-meth oxy-nicotinic acid and N-[3-(acridine-9-yl-amino)-5-hydroxymethyl-phenyl]-2-aminopropaneamide to give the titled compound.

yield: 49.1% m.p.: 231~233° C. $^1$H NMR(DMSO-$d_6$) 1.13(3H,t), 1.38(3H,d), 2.12(1H,s), 2.79(2H,q), 3.19(4H,m), 3.59(4H,m), 3.75(6H,s), 3.96(3H,s), 4.46(2H,s), 4.53(1H,m), 5.19(1H,m), 6.03(1H,s), 6.15(2H,s), 6.50(1H,s), 7.04(2H/m), 7.32(2H,s), 7.60(4H,m), 7.96(1H,s), 8.00(11H,s), 8.25(11H,m), 8.51(1H,d), 9.97(1H,s)

Example 4

4-(3,5-difluorophenyl)piperazine-1-carboxylic acid (5-{1-[3-(acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3,5-difluorophenyl)-piperazine-1-carbonyl]-amino}-6-methoxy-nicotinic acid and N-[3-(acridine-9-yl-amino)-5-hydroxymethyl-phenyl]-2-aminopropaneamide to give the titled compound.

yield: 48.7% m.p. 202~204° C. $^1$H NMR(DMSO-$d_6$): 1.20(3H,t), 1.38(3H,d), 2.78(2H,q), 3.30(4H,m), 3.59(4H,m), 3.96(3H,s), 4.45(2H,s), 4.53(1H,m), 5.20(1H,s), 6.54(2H,m), 6.69(2H,d), 7.09(2H,m), 7.33(2H,s), 7.61(4H,m), 7.94(1H,s), 8.04(1H,s), 8.25(1H,s), 8.51(1H,d), 9.99(1H,s)

Example 5

4-(3,5-dichlorophenyl)piperazine-1-carboxylic acid (5-{1-[3-(acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3,5-dichlorophenyl)-piperazine-1-carbonyl]-amino}-6-methoxy-nicotinic acid and N-[3-(acridine-9-yl-amino)-5-hydroxymethyl-phenyl]-2-aminopropaneamide to give the titled compound.

yield: 47.8% m.p.: 184~186° C. $^1$H NMR(DMSO-d$_6$): 1.20(3H,t), 1.38(3H,d), 2.79(2H,q), 3.32(4H,m), 3.59(4H, m), 3.96(3H,s), 4.46(2H,s), 4.54(11H,m), 5.18(1H,s), 6.45 (1H,s), 6.92(1H,s), 7.02(3H,s), 7.34(3H,m), 7.50(3H,m), 7.94(1H,s), 8.04(1H,s), 8.22(1H,m), 8.50(1H,m), 9.96(1H,s)

Example 6

4-(3-fluorophenyl)piperazine-1-carboxylic acid (5-{1-[3-(acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3-fluorophenyl)-piperazine-1-carbonyl]-amino}-6-methoxy-n icotinic acid and N-[3-(acridine-9-yl-amino)-5-hydroxymethyl-phenyl]-2-aminopropaneamide to give the titled compound.

yield: 53.4% m.p.: 208~210° C. $^1$H NMR(DMSO-d$_6$) 1.16(3H,t), 1.48(3H,d), 2.80(2H,q), 3.09(4H,s), 3.48(4H,m), 3.96(3H,s), 4.34(2H,s), 4.81(1H,m), 6.41(1H,m), 6.53(3H, m), 6.86(1H,m), 6.98(2H,m), 7.15(1H,m), 7.17(2H,m), 7.38 (3H,m), 7.86(3H,m), 8.35(1H,m), 9.49(1H,s)

Example 7

4-(3-hydroxyphenyl)piperazine-1-carboxylic acid (5-{1-[3-(acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3-hydroxyphenyl)-piperazine-1-carbonyl]-amino}-6-methoxy-nicotinic acid and N-[3-(acridine-9-yl-amino)-5-hydroxymethyl-phenyl]-2-aminopropaneamide to give the titled compound.

yield: 41.9% m.p. 207~209° C. $^1$H NMR(DMSO-d$_6$): 1.21(3H,t), 1.49(3H,d), 2.81(2H,q), 3.18(4H,m), 3.60(4H, m), 4.02(3H,s), 4.52(2H,s), 4.75(1H,m), 6.41(3H,m), 6.67 (1H,s), 7.06(2H,m), 7.16(2H,m), 7.24(1H,s), 7.35(1H,s), 7.47(1H,d), 7.58(2H,m), 7.86(2H,m), 8.08(2H,d), 8.36(1H, s), 9.55(1H,s)

Example 8

4-(3,4,5-trimethoxyphenyl)piperazine-1-carboxylic acid (5-{1-[3-(acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3,4,5-trimethoxyphenyl)-piperazine-1-carbonyl]-amino}-6-methoxy-nicotinic acid and N-[3-(acridine-9-yl-amino)-5-hydroxymethyl-phenyl]-2-aminopropaneamide to give the titled compound.

yield: 44.3% m.p.: 205~207° C. $^1$H NMR(DMSO-d$_6$): 1.23(3H,t), 1.50(3H,d), 2.81(2H,q), 3.76(3H,s), 3.83(6H,s), 4.05(3H,s), 4.54(2H,s), 4.73(1H,m), 6.75(2H,m), 7.20(2H, m), 7.37(1H,s), 7.41(1H,s), 7.50(1H,d), 7.66(2H,m), 7.88 (2H,m), 8.09(1H,s), 8.14(2H,m), 8.48(1H,s), 9.01(1H,s), 9.77(1H,s)

Example 9

4-(3,5-dimethoxyphenyl)piperazine-1-carboxylic acid (5-{1-[3-(acridine-9-yl-amino)-5-hydroxymethylphenylcarbamoyl]-ethylcarbamoyl}-2-methoxy-6-propylpyridine-3-yl)-amide The same reaction procedure to the example 1 were carried out using 2-propyl-5-{[4-(3,5-dimethoxyphenyl)-piperazine-1-carbonyl]-amino}-6-methoxy-nicotinic acid and N-[3-(acridine-9-yl-amino)-5-hydroxymethyl-phenyl]-2-aminopropaneamide to give the titled compound.

yield: 41.2% m.p.: 220~222° C. $^1$H NMR(DMSO-d$_6$): 0.88(3H,t), 1.38(3H,d), 1.68(2H,m), 2.76(2H,q), 3.19(4H, m), 3.59(4H,m), 3.75(6H,s), 3.95(3H,s), 4.45(2H,s), 4.54 (1H,m), 5.19(1H,s), 6.04(1H,s), 6.15(2H,s), 6.50(1H,s), 7.04(2H,m), 7.31(2H,s), 7.59(4H,m), 7.98(3H,d), 8.25(1H, m), 8.50(1H,d), 9.56(1H,s)

Example 10

4-(3,5-dimethylphenyl)piperazine-1-carboxylic acid (5-{1-[3-(acridine-9-yl-amino)-5-hydroxymethylphenylcarbamoyl]-ethylcarbamoyl}-2-methoxy-6-propylpyridine-3-yl)-amide The same reaction procedure to the example 1 were carried out using 2-propyl-5-{[4-(3,5-dimethylphenyl)-piperazine-1-carbonyl]-amino}-6-methoxy-nicotinic acid and N-[3-(acridine-9-yl-amino)-5-hydroxymethyl-phenyl]-2-aminopropaneamide to give the titled compound.

yield: 42.3% m.p. 195~197° C. $^1$H NMR(DMSO-d$_6$): 0.88(3H,t), 1.38(3H,d), 1.67(2H,m), 2.25(6H,s), 2.76(2H, m), 3.15(4H,m), 3.36(6H,s), 3.59(4H,m), 3.95(3H,s), 4.45 (2H,s), 4.54(1H,m), 5.19(1H,m), 6.49(2H,s), 6.62(2H,s), 7.05(2H,m), 7.31(2H,s), 7.58(3H,m), 7.96(3H,d), 8.23(1H, m), 8.50(1H,d), 9.96(1H,s)

Example 11

N-{1-[3-(acridine-9-yl-amino)-5-hydroxymethylphenylcarbamoyl]ethyl}-5-{[4-(3,5-dimethoxyphenyl) piperazine-1-carbothionyl]amino}-6-methoxy-2-methylnicotineamide The same reaction procedure to the example 1 were carried out using 5-{[4-(3,5-dimethoxy-phenyl)-piperazine-1-carbothionyl]-amino-2-methyl-6-methoxy-nicotinic acid and N-[3-(acridine-9-yl-amino)-5-hydroxy-methyl-phenyl]-2-aminopropaneamide to give the titled compound.

yield: 58.2% m.p.: 181~183° C. $^1$H NMR(DMSO-d$_6$): 1.40(3H,d), 2.54(3H,s), 3.28(4H,m), 3.75(6H,s), 3.90(3H,s), 4.07(4H,m), 4.45(2H,s), 4.55(1H,m), 5.18(1H,m), 6.03(1H, s), 6.15(2H,s), 6.49(1H,m), 7.03(2H,m), 7.31(3H,m), 7.60 (2H,m), 7.67(2H,m), 8.25(2H,m), 8.52(1H,d), 9.08(1H,s), 9.99(1H,s)

Example 12

N-{1-[3-(acridine-9-yl-amino)-5-hydroxymethylphenylcarbamoyl]ethyl}-5-{[4-(3,5-dimethoxyphenyl) piperazine-1-carbothionyl]amino}-2-ethyl-6-methoxynicotineamide The same reaction procedure to the example 1 were carried out using 5-{[4-(3,5-dimethoxy-phenyl)-piperazine-1-carbothionyl]-amino-2-ethyl-6-methoxy-nicotinic acid and N-[3-(acridine-9-yl-amino)-5-hydroxymethyl-phenyl]-2-aminopropaneamide to give the titled compound.

yield: 43.9% m.p.: 177~179° C. $^1$H NMR(DMSO-d$_6$): 1.20(3H,t), 1.43(3H,d), 2.82(2H,m), 3.19(2H,m), 3.29(2H, m), 3.79(6H,s), 3.93(3H,s), 4.12(4H,m), 4.38(1H,m), 4.45 (1H,m), 4.60(1H,m), 6.25(1H,s), 6.58(3H,d), 7.08(3H,m), 7.45(2H,m), 7.84(6H,m), 8.34(1H,m), 8.72(1H,s), 9.77(1H, s)

Example 13

N-{1 [3-(acridine-9-yl-amino)-5-hydroxymethylphenylcarbamoyl]ethyl}-5-{[4-(3,5-dimethoxyphenyl)piperazine-1-carbothionyl]amino}-6-methoxy-2-propylnicotineamide The same reaction procedure to the example 1 were carried out using 5-{[4-(3,5-dimethoxy-phenyl)-piperazine-1-carbothionyl]-amino-2-propyl-6-methoxy-nicotinic acid and N-[3-(acridine-9-yl-amino)-5-hydroxy-methyl-phenyl]-2-aminopropaneamide to give the titled compound.

yield 46.5% m.p.: 168–170° C. $^1$H NMR(DMSO-d$_6$): 0.90(3H,t), 1.38(3H,d), 1.69(2H,m), 2.83(2H,m), 3.28(4H, m), 3.75(6H,s), 3.91(3H,s), 4.13(4H,m), 4.46(2H,s), 4.55 (1H,m), 6.03(1H,s), 6.15(2H,s), 6.53(1H,s), 7.08(3H,m), 7.31(2H,s), 7.60(3H,m), 7.66(2H,m), 7.76–8.35(2H,m), 8.53(1H,d), 9.07(1H,s), 9.99(1H,s)

Example 14

N-{1-[3-(acridine-9-yl-amino)-5-hydroxymethylphenylcarbamoyl]ethyl}-5-{[4-(3,5-dimethylphenyl)piperazine-1-carbothionyl]amino}-2-ethyl-6-methoxy nicotineamide The same reaction procedure to the example 1 were carried out using 5-{[4-(3,5-dimethyl-phenyl)-piperazine-1-carbothionyl]-amino-2-methyl-6-methoxy-nicotinic acid and N-[3-(acridine-9-yl-amino)-5-hydroxymethyl-phenyl]-2-aminopropaneamide to give the titled compound.

yield: 47.7% m.p. 198–200° C. $^1$H NMR(DMSO-d$_6$): 1.21(3H,t), 1.41(3H,d), 2.30(6H,s), 2.82(2H,q), 3.17(2H,m), 3.27(2H,m), 3.90(3H,s), 4.07(4H,m), 4.32(2H,s), 4.45(1H, m), 4.60(1H,m), 6.25(1H,s), 6.58(3H,d), 7.08(3H,m), 7.45 (2H,m), 7.84(6H,m), 8.34(1H,m), 8.72(1H,s), 9.77(1H,s)

Example 15

4-(3,5-dimethylphenyl)-piperazine-1-carboxylic acid (6-ethyl-5-{1-[3-hydroxymethyl-5-(2-methylacridine-9-yl-amino)-phenylcarbamoyl]-ethylcarbamoyl}-2-methoxypyridine-3-yl)amide The same reaction procedure to the example 1 were carried out using 2-ethyl-5-{[4-(3,5-dimethylphenyl)-piperazine-1-carbonyl]-amino}-6-methoxy-nicotinic acid and 2-amino-N-[3-hydroxymethyl-5-(2-methyl-acridine-9-yl-amino)-phenyl]-propioneamide to give the titled compound.

yield 51.3% m.p.: 164~166° C. $^1$H NMR(DMSO-d$_6$): 1.18(3H,t), 1.52(3H,d), 2.05(1H,s), 2.17(2H,m), 2.22(11H, s), 2.28(6H,s), 2.82(2H,m), 3.10(4H,m), 3.63(4H,m), 4.00 (3H,s), 4.42(2H,s), 4.85(1H,m), 6.51(3H,m), 6.56(1H,s), 7.00(3H,m), 7.43(2H,m), 7.78(4H,m), 8.48(1H,m), 9.53(1H,s)

Example 16

4-(3,5-dimethylphenyl)piperazine-1-carboxylic acid (5-{1-[3-(3,4-dimethylacridine-9-yl-amino)-5-hydroxymethylphenylcarbamoyl]-ethylcarbamoyl}-6-ethyl-2-methoxypyridine-3-yl)amide The sane reaction procedure to the example 1 were carried out using 2-ethyl-5-{[4-(3,5-dimethylphenyl)-piperazine-1-carbonyl]-amino}-6-methoxy-nicotinic acid and 2-amino-N-[3-(3,4-dimethyl-acridine-9-yl-amino)-5-hydroxymethyl-phenyl]-propioneamide to give the titled compound.

yield 53.9% m.p.: 176~178° C. $^1$H NMR(DMSO-d$_6$): 1.21(3H,t), 1.52(3H,d), 2.28(6H,s), 2.39(3H,s), 2.74(3H,s), 2.83(2H,q), 3.05(4H,m), 3.48(4H,m), 3.99(3H,s), 4.30(2H, s), 4.89(1H,m), 6.41(1H,m), 6.49(2H,s), 6.56(1H,s), 6.85 (1H,m), 7.05(4H,m), 7.54(1H,m), 7.73(1H,m), 7.92(2H,m), 8.42(1H,s), 9.31(1H,s)

Example 17

4-(3,5-dimethylphenyl)piperazine-1-carboxylic acid (5-{1-[3-(4-methoxy-acridine-9-yl-amino)-5-hydroxymethylphenylcarbamoyl]-ethylcarbamoyl}-6-ethyl-2-methoxypyridine-3-yl)amide The same reaction procedure to the example 1 were carried out using 2-ethyl-5-{[4-(3,5-dimethylphenyl)-piperazine-1-carbonyl]-amino}-6-methoxy-nicotinic acid and 2-amino-N-[3-(4-methoxy-acridine-9-yl-amino)-5-hydroxymethyl-phenyl]-propioneamide to give the titled compound.

yield: 50.8% m.p.: 178~179° C. $^1$H NMR(DMSO-d$_6$): 1.18(3H,t), 1.50(3H,t), 2.27(6H,s), 2.82(2H,q), 3.12(4H,m), 3.53(4H,m), 3.98(3H,s), 4.14(1H,m), 4.42(2H,s), 4.81(1H, m), 6.52(4H,m), 6.89(4H,m), 7.18(2H,m), 7.41(3H,m), 7.93 (1H,m), 8.37(1H,s), 9.33(1H,s)

Example 18

4-phenyl-piperazine-1-carboxylic acid{5-[3-(acridine-9-yl-amino)-5-hydroxy-methylphenylcarbamoyl]-6-ethyl-2-methoxy-pyridine-3-yl}amide 2-ethyl-6-methoxy-5-[(4-phenylpiperazine-1-carbonyl)amino]nicotinic acid (6.48 g, 15.7 mmole) was dissolved in DMF (100 mL), thereto WSCD (3 g, 15.7 mmole) HOBT (2.12g, 15.7 mmole) and [3-(acridine-9-yl-amino)-5-aminophenyl]-methanol were added. The resulting mixture was stirred for 24 hours at the room temperature and the solvent used was removed under the reduced pressure. Then, the resulting product was purified by column chromatography to give the titled compound.

yield: 73.2% m.p.: 187~189° C. $^1$H NMR(DMSO-d$_6$): 1.24(3H,t), 2.82(2H,q), 3.02(4H,m), 3.62(4H,m), 3.99(3H, s), 4.49(2H,s), 5.28(1H,t), 6.85(2H,m), 7.02(2H,m), 7.27 (4H,m), 7.45(1H,m), 7.55(2H,m), 7.77(4H,m), 8.03(2H,s), 8.09(2H,m), 10.39(1H,s)

Example 19

4-(3,5-dimethylphenyl)-piperazine-1-carboxylic acid{5-[3-(acridine-9-yl-amino)-5-hydroxymethylphenylcarbamoyl]-6-ethyl-2-methoxy-pyridine-3-yl}amide The same reaction procedure to the example 18 were carried out using 2-ethyl-5-{[4-(3,5-dimethylphenyl)-piperazine-1-carbonyl]-amino}-6-methoxynicotinic acid and [3-(acridine-9-yl-amino)-5-aminophenyl]-methanol to give the titled compound.

yield: 69.5% m.p.: 178~180° C. $^1$H NMR(DMSO-d$_6$): 1.89(3H,t), 2.28(6H,s), 2.70(2H,q), 3.31(4H,m), 3.71(4H,m), 3.99(3H,s), 4.51(2H,s), 5.28(1H,t), 6.69(1H,s), 6.89(1H,s), 7.08(1H,s), 7.53(2H,m), 7.71(1H,s), 7.87(1H,s), 8.04(3H,m), 8.18(3H,m), 8.37(2H,m), 10.46(1H,s), 11.55(1H,s), 12.28(1H,s), 14.88(1H,s)

Example 20

4-(3,5-dimethoxyphenyl)-piperazine-1-carboxylic acid{5-[3-(acridine-9-yl-amino)-5-hydroxymethylphenylcarbamoyl]-6-ethyl-2-methoxy-pyridine-3-yl}amide The same reaction procedure to the example 18 were carried out using 2-ethyl-5-{[4-(3,5-dimethoxyphenyl)-piperazine-1-carbonyl]-amino}-6-methoxynicotinic acid and [3-(acridine-9-yl-amino)-5-aminophenyl]-methanol to give the titled compound.

yield: 70.2% m.p. 170~172° C. $^1$H NMR(DMSO-d$_6$): 1.25(3H,t), 2.84(2H,q), 3.24(4H,m), 3.66(4H,m), 3.76(6H,s) 4.04(3H,s), 4.58(2H,s), 5.28(1H,t), 6.02(1H,s), 6.08(1H,s), 6.90(1H,s), 7.26(2H,m), 7.34(1H,m), 7.42(1H,m), 7.58(1H,s), 7.62(2H,m), 7.75(2H,m), 7.88(1H,d), 8.03(2H,m), 8.23(2H,m), 8.37(1H,s), 10.06(1H,s)

Example 21

4-(3,5-difluorophenyl)-piperazine-1-carboxylic acid{5-[3-(acridine-9-yl-amino)-5-hydroxymethylphenylcarbamoyl]-6-ethyl-2-methoxy-pyridine-3-yl}amide The same reaction procedure to the example 18 were carried out using 2-ethyl-5-{[4-(3,5-difluorophenyl)-piperazine-1-carbonyl]-amino}-6-methoxynicotinic acid and [3-(acridine-9-yl-amino)-5-aminophenyl]-methanol to give the titled compound.

yield: 68.8% m.p.: 184~186° C. $^1$H NMR(DMSO-d$_6$): 1.24(3H,t), 2.79(2H,q), 3.31(4H,m), 3.59(4H,m), 3.98(3H,s), 4.47(2H,s), 5.19(1H,t), 6.53(2H,m), 6.70(2H,d), 7.07(1H,m), 7.38(3H,m), 7.51(3H,m), 8.05(3H,m), 10.23(1H,s), 10.93(1H,s)

Example 22

4-(3,5-dichlorophenyl)-piperazine-1-carboxylic acid{5-[3-(acridine-9-yl-amino)-5-hydroxymethylphenylcarbamoyl]-6-ethyl-2-methoxy-pyridine-3-yl}amide The same reaction procedure to the example 18 were carried out using 2-ethyl-5-{[4-(3,5-dichlorophenyl)-piperazine-1-carbonyl]-amino}-6-methoxynicotinic acid and [3-(acridine-9-yl-amino)-5-aminophenyl]-methanol to give the titled compound.

yield: 71.2% m.p.: 210~212° C. $^1$H NMR(DMSO-d$_6$) 1.25(3H,t), 2.83(2H,q), 3.30(4H,m), 3.66(4H,m), 4.03(3H,s), 4.53(2H,s), 5.41(1H,t), 6.63(1H,s), 6.79(3H,m), 7.11(2H,m), 7.23(1H,m), 7.42(1H,m), 7.55(4H,m), 7.71(1H,s), 8.09(2H,m), 8.32(1H,s), 9.74(1H,s)

Example 23

4-(3-fluorophenyl)-piperazine-1-carboxylic acid{5-[3-(acridine-9-yl-amino)-5-hydroxymethylphenylcarbamoyl]-6-ethyl-2-methoxy-pyridine-3-yl}amide The same reaction procedure to the example 18 were carried out using 2-ethyl-5-{[4-(3-fluorophenyl)-piperazine-1-carbonyl]-amino}-6-methoxynicotinic acid and [3-(acridine-9-yl-amino)-5-aminophenyl]-methanol to give the titled compound.

yield: 72.1% m.p.: 186~188° C. $^1$H NMR(DMSO-d$_6$): 1.25(3H,t), 2.84(2H,q), 3,28(4H,m), 3.67(4H,m), 4.04(3H,s), 4.55(2H,s), 5.39(1H,t), 6.63(2H,m), 6.69(2H,m), 7.22(4H,m), 7.33(1H,m), 7.44(1H,m), 7.63(4H,m), 8.17(2H,m), 8.37(1H,s), 9.66(1H,s)

Example 24

4-(3-hydroxyphenyl)-piperazine-1-carboxylic acid{5-[3-(acridine-9-yl-amino)-5-hydroxymethylphenylcarbamoyl]-6-ethyl-2-methoxy-pyridine-3-yl}amide The same reaction procedure to the example 18 were carried out using 2-ethyl-5-([4-(3-hydroxyphenyl)-piperazine-1-carbonyl]-amino}-6-methoxynicotinic acid and [3-(acridine-9-yl-amino)-5-aminophenyl-methanol to give the titled compound.

yield: 70.6% m.p. 196~198° C. $^1$H NMR(DMSO-d$_6$): 1.25(3H,t), 2.80(2H,q), 3.14(4H,m), 3.59(4H,m), 3.98(3H,s), 4.47(2H,s), 5.21(1H,t), 6.28(1H,d), 6.37(1H,s), 6.45(1H,d), 6.61(1H,m), 7.04(1H,t), 7.22(2H,m), 7.44(2H,m), 7.58(1H,m), 7.71(2H,m), 7.75(1H,m), 8.06(3H,m), 9.20(1H,s), 10.27(1H,s)

Example 25

4-(3,4,5-trimethoxyphenyl)-piperazine-1-carboxylic acid{5-[3-(acridine-9-yl-amino)-5-hydroxymethylphenylcarbamoyl]-6-ethyl-2-methoxy-pyridine-3-yl}amide The same reaction procedure to the example 18 were carried out using 2-ethyl-5-{[4-(3,4,5-trimethoxyphenyl)-piperazine-1-carbonyl]-amino}-6-methoxynicotinic acid and [3-(acridine-9-yl-amino)-5-aminophenyl]-methanol to give the titled compound.

yield: 66.8% m.p.: 190~192° C. $^1$H NMR(DMSO-d$_6$) 1.26(3H,t), 2.85(2H,q), 3.14(4H,m), 3.59(4H,m), 3.78(3H,s), 3.84(6H,s), 4.11(3H,s), 4.57(2H,s), 5.34(1H,t), 6.71(1H,s), 6.77(2H,s), 7.21(2H,s), 7.35(1H,m), 7.65(4H,m), 7.88(3H,m), 8.04(1H,s), 8.14(2H,m), 8.56(1H,s), 8.92(1H,s), 9.07(1H,s)

Example 26

N-(3-(acridine-9-yl-amino)-5-hydroxymethylphenyl]-5-{[4-(3,5-dimethoxyphenyl)-piperazine-1-carbothionyl]-amino}-2-ethyl-6-methoxynicotineamide The same reaction procedure to the example 18 were carried out using 5-{[4-(3,5-dimethoxyphenyl)-piperazine-1-carbonyl]-amino-2-methyl-6-met hoxynicotinic acid and [3-(acridine-9-yl-amino)-5-aminophenyl]-methanol to give the titled compound.

yield 69.8% m.p.: 176~178° C. $^1$H NMR(DMSO-ck) 1.27(3H,t), 2.90(2H,q), 3.32(4H,m), 3.99(3H,s), 4.10(4H, m), 4.53(2H,s), 5.35(1H,s), 6.03(1H,s), 6.05(2H,d), 6.61 (1H,s), 7.19(3H,m), 7.39(1H,m), 7.55(2H,m), 7.72(2H,m), 8.11(4H,m), 9.16(1H,s)

Example 27

N-(3-(acridine-9-yl-amino)-5-hydroxymethylphenyl]-5-{[4-(3,5-dimethylphenyl)-piperazine-1-carbothionyl]-amino}-2-ethyl-6-methoxynicotineamide The same reaction procedure to the example 18 were carried out using 5-{[4-(3,5-dimethylphenyl)-piperazine-1-carbothionyl]-amino-2-methyl-6-m ethoxynicotinic acid and [3-(acridine-9-yl-amino)-5-aminophenyl]-methanol to give the titled compound.

yield 71.2% m.p. 170~172° C. $^1$H NMR(DMSO-d$_6$): 1.28(3H,t), 2.27(6H,s), 2.90(2H,q), 3.28(4H,m), 3.99(3H,s), 4.11(4H,m), 4.55(2H,s), 5.39(1H,t), 6.54(3H,m), 6.70(1H, s), 7.15(2H,m), 7.32(1H,m), 7.47(1H,m), 7.60(2H,m), 7.76 (2H,m), 8.02(1H,s), 8.13(2H,m), 8.42(1H,s), 9.70(1H,s)

Example 28

N-(3-(acridine-9-yl-amino)-5-hydroxymethylphenyl]-5-{[4-(3-fluorophenyl)-piperazine-1-carbythionyl]-amino}-2-ethyl-6-methoxynicotineamide The same reaction procedure to the example 18 were carried out using 5-{[4-(3-fluorophenyl)-piperazine-1-carbonyl]-amino-2-methyl-6-methoxynicotinic acid and [3-(acridine-9-amino)-5-aminophenyl]-methanol to give the titled compound.

yield: 70.8% m.p.: 176~178° C. $^1$H NMR(DMSO-d$_6$): 1.26(3H,t), 2.87(2H,q), 3.36(4H,m), 3.94(3H,s), 4.09(4H, m), 4.46(2H,s), 5.21(1H,t), 6.61(2H,m), 6.82(2H,m), 7.26 (4H,m), 7.46(1H,s), 7.66(3H,m), 7.71(1H,s), 8.05(2H,m), 9.10(1H,s), 10.27(1H,s)

Example 29

N-(3-(acridine-9-yl-amino)-5-hydroxymethylphenyl]-5-{[4-(3,5-dichlorophenyl)-piperazine-1-carbythionyl]-amino}-2-ethyl-6-methoxynicotineamide The same reaction procedure to the example 18 were carried out using 5-{[4-(3,5-dichlorophenyl)-piperazine-1-carbothionyl]-amino-2-methyl-6-methoxynicotinic acid and [3-(acridine-9-yl-amino)-5-aminophenyl]-methanol to give the titled compound.

yield: 69.8% m.p.: 174~176° C. $^1$H NMR(DMSO-d$_6$) 1.26(3H,t), 2.86(2H,q), 3.42(4H,m), 3.93(3H1's), 4.07(4H, m), 4.47(2H,s), 5.2(1H,t), 6.54(1H,s), 6.91(1H,s), 6.99(2H, m), 7.11(2H,m), 7.43(2H,s), 7.58(3H,m), 7.72(2H,m), 8.03 (2H,m), 9.09(1H,s), 10.24(1H,s)

The compounds prepared in the examples according to the present invention were tested for pharmacological activities against tumors. Antitumor activities of the compounds were tested in vitro against 5 kinds of human tumor cell lines and 2 kinds of leukemia tumor cell lines.

Methods and results of the tests are as follows.

Experimental 1: In vitro Antitumor Effect Against Human Tumor Cell Lines.

A. Tumor Cell Lines: A549 (human non-small lung cell)
SKOV-3 (human ovarian cell)
HCT-15 (human colon cell)
XF-498 (human CNS cell)
SKMEL-2 (human melanoma cell)

B. Method: SRB Assay a. Human solid tumor cell lines, A549(non-small lung cell), SKMEL-2(melanoma), HCT-15(colon), SKOV-3(ovarian) and XF-498(CNS) were cultured in 5% $CO_2$ incubators using the RPMI 1640 media containing 10% FBS at 37° C., while with transfer-culturing successively once or twice per week. Cell cultures were dissolved in a solution of 0.25% trysin and 3 mmol CDTA PBS(−) to separate the cells sticked on the culture media.

b. $5 \times 10^3 \sim 2 \times 10^4$ cells were added into each well of 96-well plate and cultured in 5% $CO_2$ incubator at 37° C. for 24 hours.

c. Each sample drug was dissolved in a little DMSO and diluted with the used medium to a prescribed concentration for experiment, while the final concentration of DMSO was adjusted below 0.5%.

d. Medium of each well cultured for 24 hours as above b. was removed by aspiration. Each 200 μl of drug samples prepared in c. was added into each well and the wells were cultured for 48 hours. Tz(time zero) plates were collected at the point of time drugs were added.

e. According to the SRB assay method, cell fixing with TCA, staining with 0.4% SRB solution, washing with 1% acetic acid and elution of dye with 10 mmol Tris solution were carried out on Tz plates and culture-ended plates, and then, OD values were measured at 520 nm.

C. Calculation of Result a. Time zero(Tz) value was determined with measuring the SRB protein value at the point of time drugs were added.

b. Control value(C) was determined with the OD value of an well untreated with drug.

c. Drug-treated test value(T) was determined with the OD value of drug-treated well.

d. Effects of drugs were estimated with growth stimulation, net growth inhibition and net killing calculated from Tz, C and T values.

e. If $T \geq Tz$, cellular response function was calculated by $100 \times (T-Tz)/(C-Tz)$, and, if $T < Tz$, by $100 (T-Tz)/Tz$. The results are shown in the next table 1.

REFERENCE

1) P. Skehan, R. Strong, D Scudiero, A. Monks, J. B. Mcmahan, D. T. Vistica, J. Warren, H. Bokesh, S. Kenney and M. R. Boyd: Proc. Am. Assoc. Cancer Res., 30, 612 (1989).

2) L. V. Rubinstein, R. H. Shoemaker, K. D. Paull, R. M. Simon, S. Tosini, P. Skehan, D. Scudiero, A. Monks and M. R. Boyd; J. Natl. Cancer Inst, 82, 1113 (1990).

3) P. Skehan, R. Strong, D. Scudiero, A. Monks, J. B. Mcmahan, D. T. Vistica, J. Warren, HL Bokesch, S. Kenney and M. R. Boyd.; J, Natl. Cancer Inst., 82, 1107 (1990).

D. Results.

It was found that the compounds of the present invention have the even or superior antitumor activities $ED_{50}$ (μg/ml) than that of cisplatin, the control against human solid cancer cell lines.

TABLE 1

| | $ED_{50}$ (μg/ml) | | | | |
|---|---|---|---|---|---|
| Ex. No. | A549 | SK-OV-3 | SK-MEL-2 | XF-498 | HCT-15 |
| 2 | 0.12 | 0.12 | 0.01 | 0.18 | 0.19 |
| 3 | 0.12 | 0.19 | 0.03 | 0.18 | 0.13 |
| 9 | 0.24 | 0.19~ | 0.15 | 0.15 | 0.15 |
| 16 | 0.08 | 0.14 | 0.02 | 0.09 | 0.07 |
| 19 | 0.21 | 0.17 | 0.18 | 0.38 | 0.27 |
| Cisplatin | 0.81 | 0.71 | 0.71 | 0.77 | 3.03 |

Experimental 2: In Vitro Antitumor Effects Against Animal Leukemia Cells.

A. Material:

Tumor cell lines: P388 (mouse lymphoid neoplasma cell)

B. Method: Dye Exclusion Assay.

1) The concentration of P388 cells being cultured in RPMI 1640 media containing 10% FBS was adjusted to $1 \times 10^6$ cells/ml.
2) Each sample drug of a concentration diluted in the ratio of log dose was added into cell culture media and cultured at 37 t for 48 hours in 50% $CO_2$ incubator, and then viable cell number was measured by dye exclusion test using trypan blue.
3) The concentration of each sample compound showing 50% cell growth inhibition($IC_{50}$) compared with the control was determined and listed in the table 2 below.

REFERENCE

1) P. Skehan, R. Strong, D. Scudiero, A. Monks, J. B. Mcmahan, D. T. Vistica, J. Warren, I Bokesch, S. Kenney and M. R. Boyd.: Proc. A. L Assoc. Cancer Res., 30, 612 (1989).
2) L. V. Rubinstein, R. H. Shoemaker, K D. Paull, R. M. Simon, S. Tosini, P. Skehan, D. Scudiero, A. Monks and M. R. Boyd.: J. Natl. Cancer Inst, 82, 1113 (1990)
3) P. Skehan, R. Strong, D. Scudiero, J. B. Mcmahan, D. T. Vistica, J. Warren, H. Bokesch, S. Kenney and M. R. Boyd.: J. Natl. Cancer Inst., 82, 1107(1990)

C. Results

As the result of measurement of antitumor activities $IC_{50}$(μg/ml) against P388 mouse cancer cells of the compounds according to the present invention, it was found that the compounds tested have equal to or higher antitumor activities than those of the control drug, mitomycin C.

TABLE 2

| Ex. No. | P388 (μg/ml) |
|---|---|
| 2 | 0.3 |
| 3 | 1.0 |
| 4 | 0.9 |

TABLE 2-continued

| Ex. No. | P388 (μg/ml) |
|---|---|
| 9 | 0.4 |
| 16 | 0.3 |
| Mitomycin C | 1.1 |

Experimental 3: In Vivo Antitumor Effects Against Mouse Leukemia P388 Cells

A. Material of Experiment

BDF1 mice were used.

B. Method of Experiment

1) Leukemia P388 cells being transfer-cultured successively in DBA/2 mouse, were grafted into each mouse of a group comprising 8 mice of 6 week old BDF1 mouse with the dose of $1 \times 10^6$ cells/0.1 ml
2) Sample drugs were dissolved in PBS or suspended in 0.5% tween 80, and then injected into abdominal cavity of mouse at each prescribed concentration on days 1, 5, 9, respectively.
3) With observation everyday, survival times of tested mice were measured. Antitumor activities was determined in such a manner that the increasing ratio (T/C %) of average survival days of drug-treated groups compared with the control group was calculated using the mean survival times of each tested groups.

The results are shown at the next table 3.

TABLE 3

| Ex. No. | Dose (mg/kg) | MST (days) | T/C (%) |
|---|---|---|---|
| 2 | 100 | 22.0 | 200.0 |
| | 50 | >60.0 | >545.5 |
| | 25 | >60.0 | >545.5 |
| 3 | 100 | 11.6 | 100.0 |
| | 50 | >60.0 | >545.5 |
| | 25 | 17.0 | 154.5 |

Experimental 4. Acute Toxicity Test ($LD_{50}$):

a) Method: Litchfield-Wilcoxon Method.

6-week-old ICR mice (male 30±2.0 g) were fed freely with solid feed and water at room temperature, 23±1° C. and at humidity 60±5%. Sample drugs were injected into the abdominal cavities of mice. Each group comprised 6 mice. Observed during 14 days, external appearances and life or death thereof were recorded, and also, visible lesions were observed from dead mice by dissection. $LD_{50}$ value was calculated by Litchfield-wilcoxon method.

b) Results

As shown in the following table, the compounds according to the present invention are predominantly safe in comparison with cisplatin, whereby much problems of known compounds such as restriction of dosage, unfavorable side effects by toxicity, etc. may be overcome considerably.

TABLE 4

| Ex. No. | LD$_{50}$ (mg/kg) | |
| --- | --- | --- |
| | ip | iv |
| 2 | | 80 |
| 3 | | 80 |
| Cisplatin | 9.7 | |

As described above, the compounds according to the present invention are much more safer and also have much superior antitumor activities to known anticancer drugs, and accordingly the compounds are expected to be useful as a new anticancer drug.

The invention claimed is:

1. A compound of the formula (I)

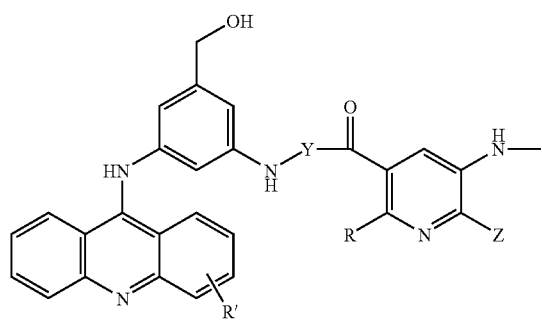

-continued

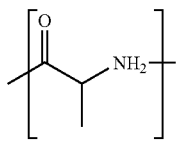

wherein Y is a bond or

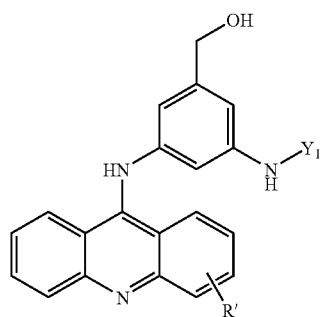

wherein X is oxygen or sulfur, $R_1$, $R_2$, $R_3$, $R_4$ and $R_5$ are independently hydrogen, halogen, nitro, amino, hydroxyl, $C_1$–$C_4$ lower alkylamino, $C_1$–$C_4$ alkyl or $C_1$–$C_4$ lower alkoxy, R' and R" are independently $C_1$–$C_4$ alkyl or $C_1$–$C_4$ lower alkoxy, and Z is $C_1$–$C_4$ lower alkyl, $C_1$–$C_4$ lower alkoxy or $C_1$–$C_4$ lower alkylamino or pharmaceutically acceptable salt thereof.

2. A process for the preparation of a compound of the formula (I) or pharmaceutically acceptable salt thereof comprising reacting a compound of the formula (a) with a compound of the formula (b) in the presence of a condensing agent and an acid in an organic solvent to give a compound of the formula (I) and if necessary converting the compound of the formula (I) into the pharmaceutically acceptable salt thereof:

(I)

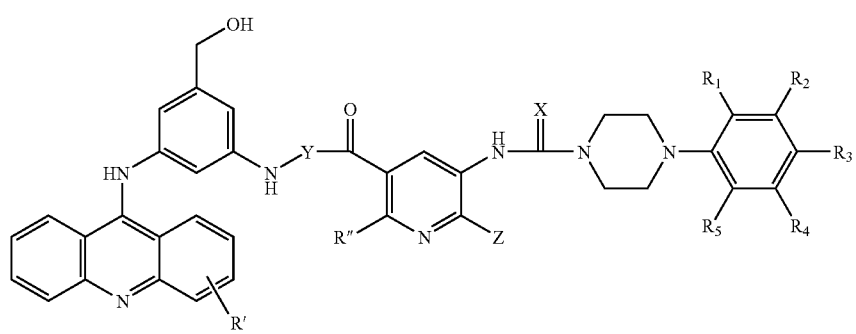

(a)

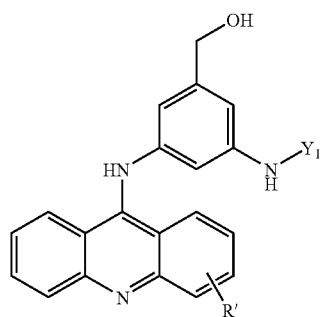

(b)

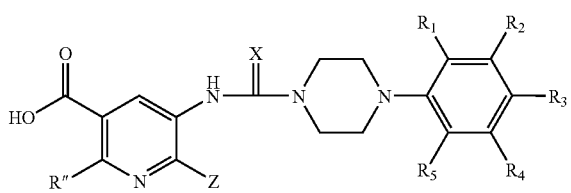

wherein $R_1$, $R_2$, $R_3$, $R_4$, $R_5$, R', R", X, Y and Z are as defined in claim 1 and

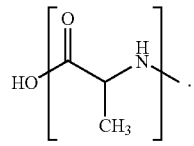

$Y_1$ is hydrogen or the group of

3. A process for the preparation of a compound of the formula (I) or pharmaceutically acceptable salt thereof comprising reacting a compound of the formula (c) with a compound of the formula (d) in the presence of a condensing agent and an acid in an oroanic solvent to give a compound of the formula (I) and if necessary converting the compound of the formula (I) into the pharmaceutically acceptable salt thereof:

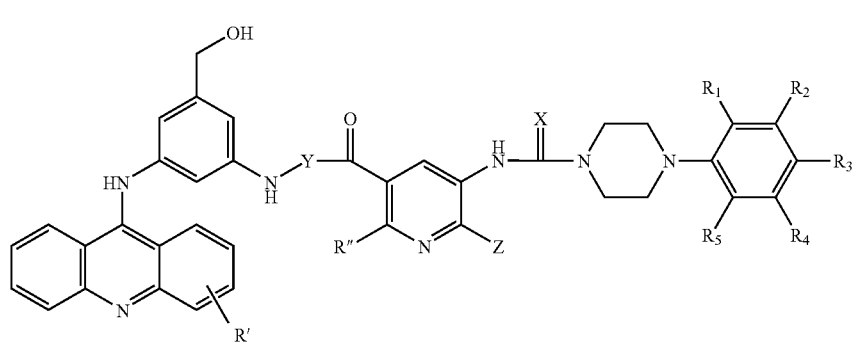

(I)

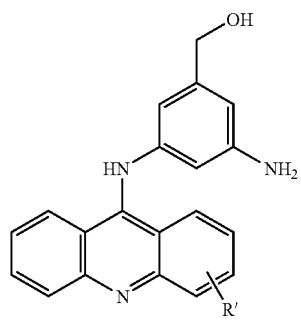

(c)

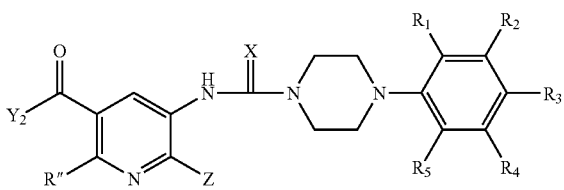

(d)

wherein $R_1$, $R_2$, $R_3$, $R_4$, $R_5$, R', R", X, Y and Z are as defined in claim 1 and $Y_2$ is —OH or the group of

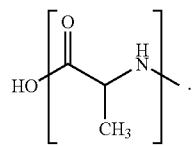

* * * * *